United States Patent [19]

Dumont et al.

[11] Patent Number: 4,950,663

[45] Date of Patent: Aug. 21, 1990

[54] ANTIHYPERTENSIVE COMPOSITION

[76] Inventors: Louis Dumont, 1530 Algonquin, Fabreville, Québec, Canada, H7P 4R6; Gilles Caillé, 1098 Pl. Pierre Dupaigne, Montréal, Québec, Canada, H2M 2S5

[21] Appl. No.: 310,918

[22] Filed: Feb. 15, 1989

[51] Int. Cl.$^5$ .............................................. A61K 31/55
[52] U.S. Cl. ................................................... 514/211
[58] Field of Search ......................................... 514/211

[56] References Cited

U.S. PATENT DOCUMENTS 3,562,257  2/1971  Kugita et al. ...................... 514/929

OTHER PUBLICATIONS

J. Cardiovasc. Pharmacol., vol. 7, No. 1, 1985, pp. 152–157.
Seiyaku; C.A., vol. 96, (1982), 149164w.
Journal of Cardiovascular Pharmacology, 7; 152-157—H. Yabana et al., (1985).

Primary Examiner—Allen J. Robinson
Attorney, Agent, or Firm—Cushman, Darby & Cushman

[57] ABSTRACT

The present invention relates to an antihypertensive composition comprising N-desmethyl, deacetyl diltiazem in association with a pharmaceutically acceptable carrier.

3 Claims, No Drawings

ANTIHYPERTENSIVE COMPOSITION

FIELD OF THE INVENTION

The present invention relates to a novel composition particularly suitable use in the treatment of hypertension or as a peripheriphal vasodilator and to a method for reducing hypertension.

PRIOR ART

Diltiazem, which is the generic name for (+)-cis-3-(acetyloxy)-5-[2-dimethylamino-ethyl]-2,3-dihydro-2-(4-methoxyphenyl)-1,5-benzothiaz epin-4(5H)one monohydrochloride, is presently one of the leading products prescribed when a calcium antagonist is required.

Diltiazem is a calcium ion influx inhibitor (calcium entry blocker or calcium ion antagonist). The anti-anginal effect of this group of drugs is believed to be related to their specific cellular action of selectively inhibiting the transmembrane influx of calcium ions into cardiac muscle and vascular smooth muscle. The contractile processes of these tissues are dependent upon the movement of extracellular calcium into the cells through specific ion channels. Diltiazem blocks the transmembrane influx of calcium through the slow channel without affecting to any significant degree the transmembrane influx of sodium through the fast channel. This results in a reduction of free calcium ions available within cells of the above tissues. Diltiazem does not alter total serum calcium.

The precise mechanism by which diltiazem relieves angina has not been fully determined, but it is believed to be brought about largely by its vasodilator action.

In angina due to coronary spasm, diltiazem increases myocardial oxygen delivery by dilating both large and small coronary arteries and by inhibiting coronary spasm at drug levels which cause little negative inotropic effect. The resultant increases in coronary blood flow are accompanied by dose-dependent decreases in systemic blood pressure and decreases in peripheral resistance.

In angina of effort it appears that the action of diltiazem is related to the reduction of myocardial oxygen demand. This is probably caused by a decrease in blood pressure brought about by the reduction of peripheral resistance and of heart rate.

Studies to date, primarily in patients with good ventricular function, show that cardiac output, ejection fraction, and left ventricular end-diastolic pressure have not been affected. Resting heart rate is usually slightly reduced by diltiazem. In humans, i.v. diltiazem in doses of 20 mg prolongs AH conduction time and AV node functional and effective refractory periods by approximately 20%. In patients with sick sinus syndrome, diltiazem significantly prolongs sinus cycle length (up to 50% in some cases). Chronic oral administration of diltiazem in doses up to 360 mg per day has resulted in small increases in PR interval.

For the management of angina resulting from coronary artery spasm and for the management of chronic stable angina (effort-associated angina) without evidence of vasospasm patients who remain symptomatic despite adequate doses of beta-blockers and/or organic nitrates or who cannot tolerate those agents.

Diltiazem may be useful in unstable angina when spasm of the coronary vessels is definitely a contributing factor (e.g. S-T segment elevation). If there is no objective evidence of a spastic component then nitrates or nitrates plus a beta-blocker are, at present, the treatment of choice. If in the view of a cardiologist, the addition of diltiazem to this regimen is considered necessary and safe, then the use of diltiazem might be considered. Generally, the patient should be hospitalized and treatment initiated under the supervision of a cardiologist.

Diltiazem may be used in combination with beta-adrenergic blocking drugs in chronic stable angina in patients with normal ventricular function, but available information is not sufficient to predict with confidence the effects of concurrent treatment. When such concomitant therapy is introduced patients must be monitored closely.

Patients with sick sinus syndrome except in the presence of a functioning ventricular pacemaker; patients with second or third degree AV block; patients with a hypersensivity to diltiazem; and, patients with severe hypotension (less than 90 mm Hg systolic).

Cardiac conduction: Diltiazem prolongs AV node refractory periods without significantly prolonging sinus node recovery time, except in patients with sick sinus syndrome. Concomitant use of diltiazem with beta-blockers or digitalis glycosides may result in additive effects on cardiac conduction or heart rate. Congestive heart failure: Because diltiazem has a negative inotropic effect and it affects cardiac conduction, the drug should be used with caution and under careful supervision in patients with congestive cardiac failure.

Generally, diltiazem should not be given to patients with impaired left ventricular function while they receive beta-blockers.

Diltiazem gives no protection against the dangers of abrupt beta-blocker withdrawal and such withdrawal should be done by the gradual reduction of the dose of beta-blocker.

It is also known that diltiazem decreases the heart rate to some degree which is a disadvantage or a drawback for patients on antiarrythmic drug therapy. It is also known that in conditions of ischemic heart arrest, calcium antagonist is recommended.

Diltiazem related products or metabolites have been disclosed in J. Cardiovasc. Pharmacol, vol. 7, No. 1, 1985:152–157 wherein the cardiovascular effects of the metabolites of diltiazem in dogs are discussed. This article discloses as one of the metabolites the N-desmethyl, deacetyl diltiazem. After carrying out comparative test between diltiazem and N-desmethyl deacetyl diltiazem to determine the dose required to cause a 50% increase in blood flow showed that the N-desmethyl, deacetyl diltiazem represented only 20% (1/5) of the effect diltiazem on coronary blood flow. Furthermore, there is no evidence on suggestion in this article that beneficial effect could be obtained if higher doses of N-desmethyl, deacetyl diltiazem were administered. It would thus appear that it could be desirable to provide a diltiazem-related product which would possess some of the highly desirable properties of diltiazem while being devoid of certain of its undesirable properties and having certain other of its disadvantageous properties reduced to a certain degree.

STATEMENT OF THE INVENTION

In accordance with the present invention it has surprisingly been found that a specific metabolite of diltiazem, namely, the N-desmethyl, deacetyl diltiazem, will decrease the heart rate to a lesser degree than diltiazem so that it can be administered to patients on antiarrythmic drug or on patients where a decrease in heart rate is not desirable therapy while retaining the calcium ion antagonist properties of diltiazem. The metabolite of diltiazem of the present invention can thus be used in cardiac patients in which reduction of the heart rate is contraindicated.

The invention also provides a method for reducing or alleviating hypertension by the administration of a therapeutic dose of N-desmethyl, deacetyl diltiazem to a person afflicted with hypertension.

It has also been found that compositions containing N-desmethyl, deacetyl diltiazem are also characterized by having less side effects than diltiazem and a shorter elimination half life. The composition of the present invention unexpectedly enables the treatment of patients also taking antiarrythmic drugs because of a much smaller accumulation at the level of the conductive tissues, due to its lower liposolubility than diltiazem and its short term effect.

The fact that the composition of the present invention is not metabolized extensively by the liver and then excreted by the kidney and bile, renders possible the treatment of hypertension of patients having impaired hepatic or renal functions. Another advantage of the shorter elimination half life of the product of the present invention lies in its reduced toxicity and the decreased probability of an overdosage compared to diltiazem.

The N-desmethyl, deacetyl diltiazem used in the present invention is prepared by reacting 2-(N-desmethylaminoethyl)thiophenyl with methyl 4-methoxyphenylglycidate and the reaction product is hydrolyzed and cyclized in accordance with the procedure described in Chem. Pharm. Bull. 19, 595-602 (1971) to yield the desired compound. The following Flowsheet illustrates the reaction scheme.

FLOWSHEET

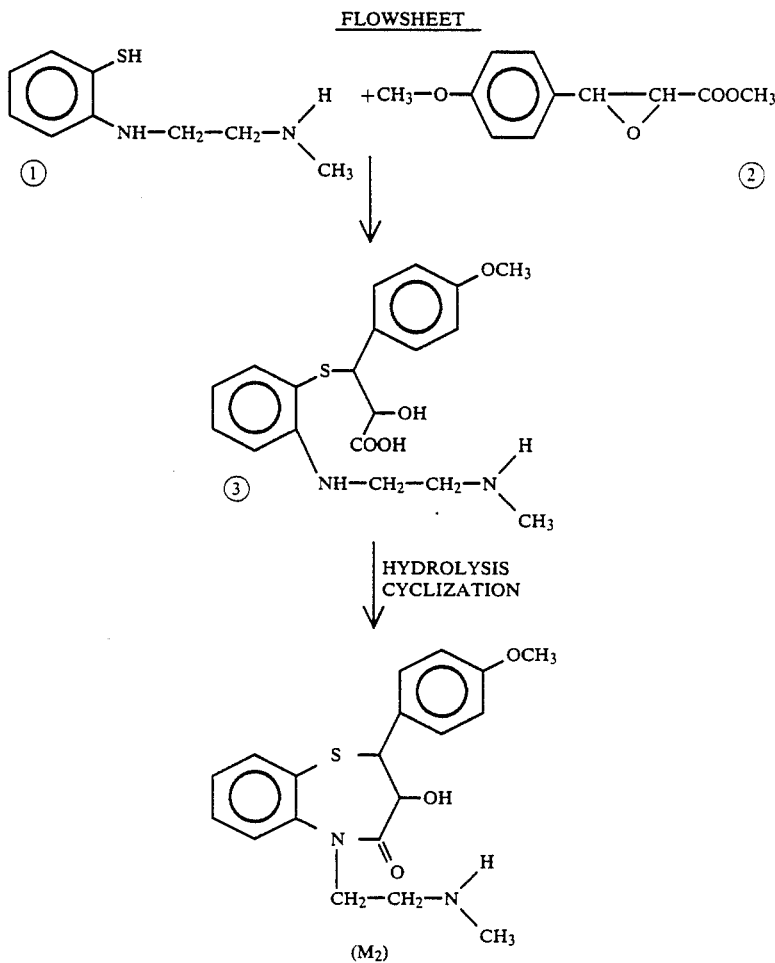

In order to establish that N-desmethyl, deacetyl diltiazem decreases the heart rate to lesser degree than diltiazem and thus can be used where reduction of the heart rate is contraindicated, tests were carried with both compounds to compare their effects on heart rate, mean arterial pressure and coronary blood flow at intravenous dosages of 0 to 1600 μg/kg. Results are reported in Table I.

TABLE I

| Comparative Cardiovascular Effects of Diltiazem (D) and N-Desmethyl, Deacetyl Diltiazem ($M_2$)* | | | | | | | | |
|---|---|---|---|---|---|---|---|---|
| Dosage (μg/kg) | | 0 | 15 | 50 | 200 | 400 | 800 | 1600 |
| Heart rate (beats/minute) | D | 130 | 134 | 131 | 122 | 105 | — | — |
|  | $M_2$ | 127 | — | 127 | 127 | — | 125 | 119 |
| Mean arterial pressure (mm Hg) | D | 99 | 94 | 84 | 67 | 58 | — | — |
|  | $M_2$ | 99 | — | 96 | 88 | — | 74 | 63 |
| Coronary blood flow (mL/minute) | D | 59 | 67 | 73 | 91 | 83 | — | — |
|  | $M_2$ | 49 | — | 53 | 55 | — | 61 | 61 |

*Experiments carried out in anesthetized dogs.

The above mentioned data indicate the specificity of $M_2$ over diltiazem. Looking at heart rate changes it can be seen that diltiazem induces >20% reduction while $M_2$, at a dosage 4 times greater, only slightly affects heart rate (<10%). Maximal reduction in mean arterial pressure was obtained with both diltiazem (−38%) and $M_2$ (−36%). The greater efficacy of diltiazem upon coronary blood flow dilation is as follows: Diltiazem increased blood flow by >50% while $M_2$ has about half that effect (>25%).

Therefore $M_2$ has equivalent peripheral dilation capacity but is devoted of major effect upon heart rate. The coronary dilation capacity of $M_2$ is about half that of diltiazem. In addition, $M_2$ was given at maximal dosage 4 times greater than diltiazem without serious cardiovascular adverse effects.

It will also be noted that in the test to determine the mean arterial pressure after administration of each compound at various dosages, the N-desmethyl, deacetyl diltiazem unexpectedly decreases the mean arterial pressure thereby confirming its high value in the treatment of hypertension.

Furthermore the N-desmethyl, deacetyl diltiazem is useful to decrease the blood pressure or the mean arterial pressure at intravenous dosages of from 200 to 1600 μg/kg. It will be noted from Table I that at 1600 μg/kg N-desmethyl, deacetyl diltiazem causes only a slight effect on the heart rate while diltiazem at 400 μg/kg had a significant effect on the heart rate.

It is also noted that N-desmethyl, deacetyl diltiazem is unexpectedly suitable for use as a coronary dilator at intravenous dosages of from 50 to 1600 μg/kg.

Preparation of N-desmethyl, deacetyl diltiazem

A mixture of 2-(N-desmethylaminoethyl)thiophenyl (7.5 g) and methyl 3-(4-methoxyphenyl)glycidate (6.7 g) was heated with stirring for 3 hours at 130°-140° C. under nitrogen. The reaction was cooled, dissolved in ether and extracted with 10% HCl. The aqueous layer was neutralized with $K_2CO_3$ and extracted with ether. The extract was washed with water and dried over $Na_2SO_4$. Evaporation of the solvent gave an oily product which was chromatographed on $Al_2O_3$.

After elution with benzene, the reaction product was mixed with 1N NaOH (15 ml) and ethanol (3 ml) and heated for 3 hours over a steam bath. Evaporation of the solvent and then neutralization with acetic acid gave a solid product was suspended in xylene and refluxed for 20 hours. After evaporation of the solvent under reduced pressure there was obtained the N-desmethyl, deacetyl diltiazem having a m.p. of 200°-205° C.

What is claimed is:

1. A method for reducing hypertension which comprises administering to an individual suffering from hypertension a therapeutic dose of N-desmethyl, deacetyl diltiazem, said therapeutic dose being at least 800 mg/day when administered orally or at least 200 μg/kg when administered intravenously.

2. The method of claim 1, wherein the product is administered orally in a dosage of from 800 to 1600 mg/day.

3. The method of claim 1, wherein the product is administered intravenously in a dosage of from 200to 1600 μg/kg.

* * * * *